United States Patent [19]

Murata et al.

[11] Patent Number: 4,522,060
[45] Date of Patent: Jun. 11, 1985

[54] DRY/DEW/FROST SENSOR

[75] Inventors: Michihiro Murata, Kyoto; Shoichi Kitao, Otokuni, both of Japan

[73] Assignee: Murata Manufacturing Co., Ltd., Japan

[21] Appl. No.: 477,410

[22] Filed: Mar. 21, 1983

[30] Foreign Application Priority Data

Mar. 24, 1982 [JP] Japan .................. 57-48415

[51] Int. Cl.³ .............. G01N 27/30; G01W 1/00
[52] U.S. Cl. .................. 73/336.5; 324/65 R
[58] Field of Search ............ 73/336.5, 335, 73; 338/34, 35

[56] References Cited

U.S. PATENT DOCUMENTS

| 2,647,238 | 7/1953 | Pear, Jr. | 73/336.5 |
| 3,287,974 | 11/1966 | Cemochowski | 73/336.5 |
| 3,422,677 | 6/1969 | Lockwood | 73/336.5 |
| 3,540,278 | 11/1970 | Diamond et al. | 73/336.5 |
| 3,676,820 | 7/1970 | Taguche | 338/34 |
| 3,900,815 | 8/1975 | Taguche | 338/34 |
| 4,007,435 | 2/1977 | Tien | 338/34 |
| 4,419,889 | 12/1983 | Muto et al. | 73/336.5 |

Primary Examiner—Daniel M. Yasich
Attorney, Agent, or Firm—Ostrolenk, Faber, Gerb & Soffen

[57] ABSTRACT

A dry/dew/frost sensor comprising a plurality of sensor units, each sensor unit comprising a ceramic substrate (1, 2) whose permittivity is lower than ice and a pair of electrodes (3, 4; 5, 6) being arranged on the ceramic substrate in contact therewith, wherein adjacent sensor units are arranged so as to face each other at a predetermined distance so that the pair of electrodes (3, 4; 5, 6) may be opposed to each other, and the impedance between the pair of electrodes on each of the sensor unit varying with changes in three states, dry, bedewed, and frosted states.

7 Claims, 11 Drawing Figures

4,522,060

DRY/DEW/FROST SENSOR

BACKGROUND OF THE INVENTION

1. Field of the Invention

The present invention relates to a dry/dew/frost sensor detecting three states (the dry, bedewed, and frosted states) as variations in impedance.

2. Description of the Prior Art

In the use of electrical equipment, moisture control is a difficult problem and thus development of an excellent moisture sensor has been demanded. With certain apparatus, deterioration in characteristics caused by frost as well as that caused by moisture is a serious problem. In the operation of refrigerating equipment, for example, the efficiency is reduced when frost forms on the equipment, and therefore, defrosting becomes necessary. Thus, development of a sensor to detect frosted state has also been demanded.

Hitherto, such a dew sensor, for example, utilizing the variations in resistance resulting from dew formation, and some other types have been developed. Meanwhile, as for frost sensors, such a type as utilizing the change in resonant frequency of a resonating body due to frost formation thereon has been produced. Nothing, however, has been produced to detect both dew and frost, or to discern three states (dry, bedewed, and frosted) with a single sensor. Therefore, in order to detect which of the three states (dry, bedewed, or frosted states) the equipment is in, it has been necessary to use at least two independent sensors, and this has made the equipment complicated.

SUMMARY OF THE INVENTION

The present invention, in summary, is a dry/dew/frost sensor comprising a plurality of sensor units, each of the sensor units comprising a sensing element whose permittivity is lower than ice and a pair of electrodes being arranged on at least one surface of the sensing element in contact therewith, wherein impedance between the pair of electrodes of each sensor unit varies with changes in three states, dried, bedewed, and frosted states indicating a maximum value in the (dry states) indicating a minimum value in the bedewed state, and indicating a medium value in said frosted state, and adjacent units of the sensing units being arranged so as to face each other at a predetermined distance so that the pairs of electrodes may be opposed to each other. Preferably, the sensing element is a ceramic substrate, and the electrodes are arranged on the ceramic substrate.

In a preferred embodiment, such material for a sensing element is selected that the impedance between the electrodes may be determined most greatly contributed by resistivity and permittivity of the sensing in the dry state, most greatly contributed by permittivity of ice in the frosted sate, and most greatly contributed by ionic conduction in water in the bedewed state.

A primary object of the present invention is to provide a dry/dew/frost sensor capable of correctly detecting three states (dry, bedewed, and frosted states) only with a single sensor.

Other objects and characteristics of the present invention will be made more apparant from the description given below with reference to accompanying drawings.

BRIEF DESCRIPTION OF THE DRAWINGS

FIG. 2 is a perspective view showing a manufacturing process, FIG. 3 is a longitudinal sectional view of a dry/dew/frost sensor, FIGS. 4 and 5 are plan views explaining a pattern of a pair of electrodes.

DESCRIPTION OF THE PREFERRED EMBODIMENTS

Figure 1:
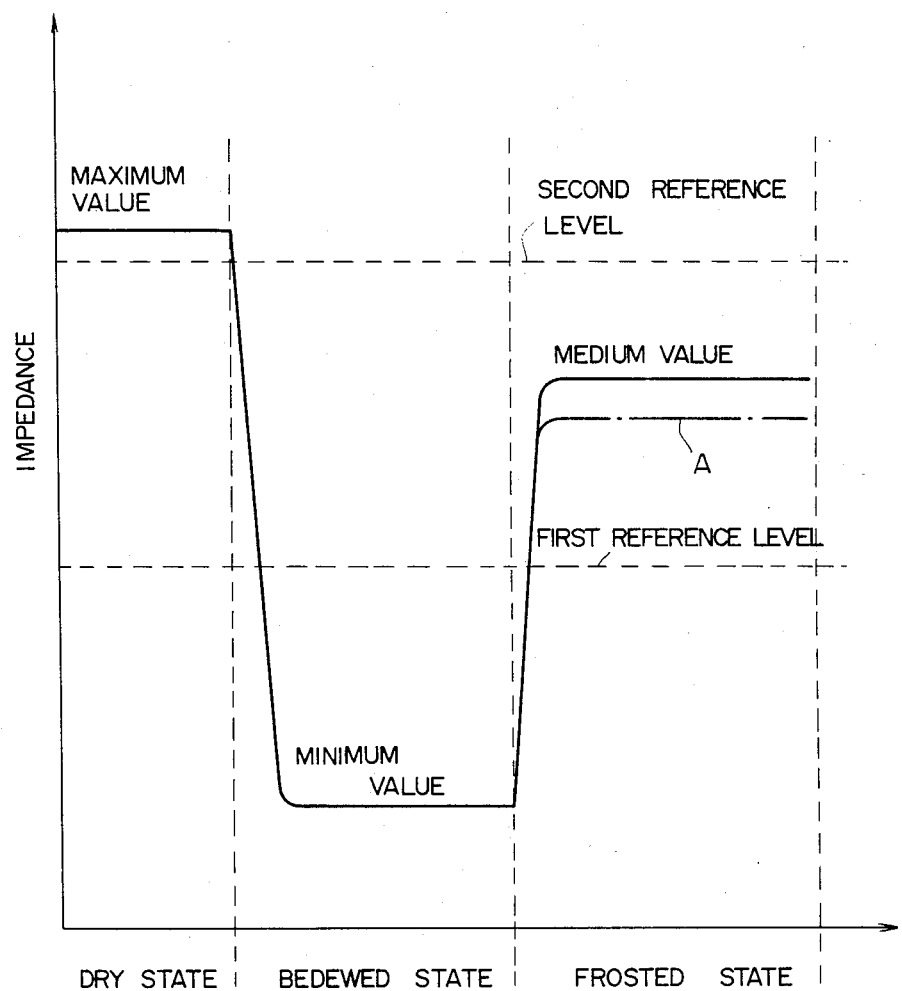
FIG. 1 is a graph indicating variations in the impedance of the sensing element used in the present invention in dry, bedewed, and frosted states.

The present invention utilizes a plurality of sensor units each comprising a sensing element whose impedance varies with changes in three states: the dry, bedewed, and frosted states. FIG. 1 is a graph indicating variations in the impedance of the sensor element used in the present invention. As apparent from FIG. 1, the sensor element of the sensor used in the present invention exhibits different values of impedance, such as a maximum impedance in the dry state; a medium impedance, relatively lower than that in the dry state, in the frosted state, and a minimum impedance lower than that in the frosted states in the bedewed state. The sensor of the present invention is obtained by arranging a plurality of such sensor units so as to face each other at a predetermined distance.

The operating principle will be made clear by the following explanation of the construction of an embodiment of the dry/dew/frost sensor of the present invention with reference to FIGS. 2 through 5.

Figure 2:
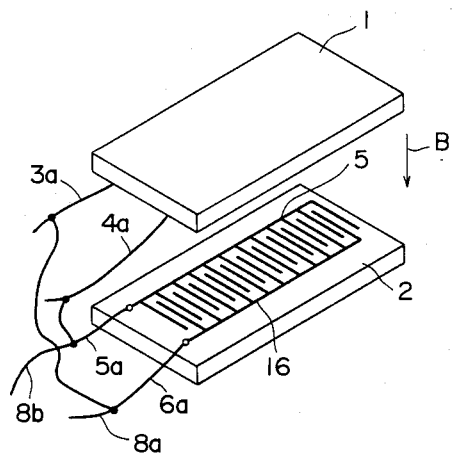
FIGS. 2 through 5 are drawings showing construction of one embodiment of the present invention, where
Figure 3:
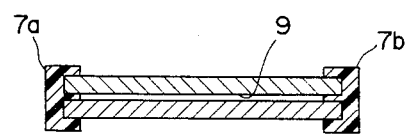
Figure 4:
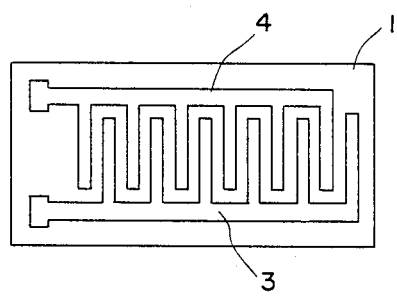

Referring to FIG. 2, ceramic plates 1, 2 which defines sensing elements are prepared. On the bottom surface of the ceramic plate 1 are arranged a pair of comb-shaped opposing electrodes 3, 4 as indicated in the plan view of FIG. 4. In the similar way, a pair of comb-shaped opposing electrodes 5, 6 are also arranged on the top surface of the ceramic plate 2. The ceramic plate 1 with the comb-shaped opposing electrodes 3, 4 thereon may be turned over keeping its direction as indicated in FIG. 4 and moved in the direction B as indicated in FIG. 2 toward the ceramic plate 2. Then plates 1 and 2 are held by insulating spacers 7a, 7b so as to oppose each other at a predetermined distance. This arrangement is shown with a longitudinal sectional view in FIG. 3. Though it is not particularly shown in FIG. 3, but as apparent from FIG. 2, the lead wire 3a attached to the comb-shaped opposing electrode 3 on one ceramic plate 1 is connected with the lead wire 6a which is attached to the comb-shaped electrode 6 on the other ceramic plate 2 and thereby one lead section 8a of the dry/dew/frost sensor is formed. Similarly, the lead wire 4a attached to the comb-shaped opposing electrode 4 on the ceramic plate 1 is electrically connected with the lead wire 5a which is attached to comb-shaped opposing electrode 5 on the ceramic plate 2, and thereby the other lead section 8b is formed. Thus a concrete example of the dry/dew/frost sensor of this embodiment is completed. As apparent from FIG. 3, one ceramic plate 1 and the other ceramic plate 2 are arranged so as to oppose each other at a predetermined distance, and thereby the pairs of comb-shaped opposing electrodes arranged on both of the ceramic plates 1 and 2 are arranged so as to oppose each other. Here, the comb-shaped opposing electrodes 3 and 5, and the comb-shaped opposing electrodes 4 and 6 are both in an opposing position, where the positional relation between the opposing comb teeth may be either directly opposite or diagonally opposite. In the embodiment explained with reference to FIGS. 2 through 5, the sensor unit made up of the ceramic plate 1 (a sensor element) and a pair of the comb-shaped opposing electrodes 3, 4 and the sensor unit made up of the ceramic plate 2 (a sensor element) and a pair of comb-shaped opposing electrodes 5, 6 are arranged so as to oppose each other with a predetermined distance maintained therebetween to define a dry/dew/frost sensor which can detect the state (dry, bedewed, or frosted) of the environment located in the space 9 defined by the predetermined distance between plates 1 and 2 (FIG. 3).

In the dry state, there is only air in the space 9, and therefore, the impedance between the lead sections 8a and 8b depends on the impedances between the comb-shaped opposing electrodes on the individual sensors. To be more specific, the impedance between the lead sections 8a and 8b depends on the impedances and permittivity of the ceramic plates 1 and 2. In the bedewed state, the inside surfaces of the ceramic plates 1, 2 (the inside surfaces here mean those open to the space 9) will have waterdrops from dew deposited thereon. Meanwhile, the ceramic plates 1, 2 are made of such material that may, as will be described later, when water drops form thereon and cause ions to flow out into the water drops, and therefore, ions will flow out into the water drops, causing electric currents due to ionic conduction to flow, and thus the impedance value between the pair of comb-shaped opposing electrodes on each individual sensor will become very small. In the event of heavy dew the space will be entirely filled with water drops, producing a conductive state between the lead sections 8a and 8b, and thus bring down the impedance between them to a minimum value. Further, in the frosted state, the space 9 will be filled with ice from the frost. Therefore, the impedance between the lead sections 8a and 8b will depend on the impedance between the pair of comb-shaped opposing elements on one sensor, the impedance of the pair of comb-shaped electrodes on the other sensor, and the impedance of the ice existing between both sensors. In the mean time, since the ceramic plates 1, 2 as sensing elements of the present invention have lower permitivity than ice, the impedance between the pair of the comb-shaped opposing electrodes on each individual sensor is determined chiefly by the permittivity of ice. Accordingly, the impedance of the dry/dew/frost sensor, or the impedance between the lead sections 8a and 8b, in the frosted state becomes rather lower than the impedance value in the dry state. In the embodiment thus far explained with reference to FIGS. 2 through 5, the variations in the impedance with changes in the three states (dry, bedewed, and frosted) are as indicated with the chain line A in FIG. 1. Therefore, it is possible to detect the three states with the variations in the impedance between the lead sections 8a and 8b. By arranging sensors to oppose each other, in particular, it is possible to lower the impedance in the frosted state a great deal.

Figure 5:
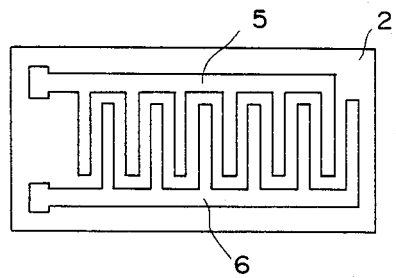
Figure 6:
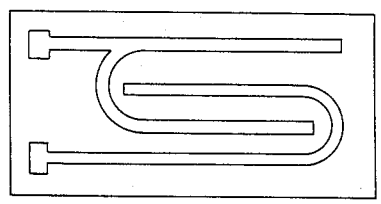
FIGS. 6 and 7 are plan views indicating a variation of the pattern of the pair of electrodes used in another embodiment of the present invention.
Figure 7:
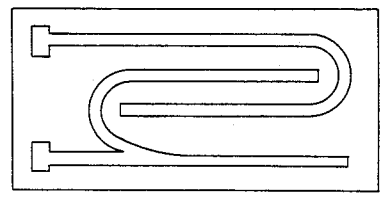

The above-stated another embodiment of the dry/dew/frost sensor of the present invention is not limited to that illustrated in the drawings and can be constructed in various ways. The pair of electrodes arranged on the ceramic plates 1, 2 as sensing elements in contact therewith, for example, can not only be of comb-shaped opposing electrodes as illustrated in FIGS. 4 and 5 but also be opposing electrodes of other shapes as illustrated in FIGS. 6 and 7, or be opposing electrodes of other plane shapes. In the case of the opposing electrodes as illustrated in FIGS. 6 and 7, the ceramic plate in FIG. 6 may be turned over and arranged so as to oppose the ceramic plate in FIG. 7 at a predetermined distance. In this example, the opposing electrodes in FIG. 6 is arranged above the opposing electrodes in FIG. 7 with the symmetrical relationship maintained. Further, in the construction examples illustrated with the drawings, the dry/dew/frost sensors composed of two sensors only were explained, but they can be composed of three or more sensors. In the case of the dry/dew/frost sensor composed of three or more sensors, the interposed sensor is preferably to be arranged with a pair of electrodes placed on each surface of the sensing element thereof.

The sensing element to be used in the present invention can be of any material so long as it has lower permittivity than ice and is capable, in a bedewed state, of inducing ions in waterdrops. To be concrete, such material will be used that is mainly composed of titanium complex oxides of ilmenite type crystal structure, like $MgTiO_3$, $ZnTiO_3$, or $FeTiO_3$, or dielectric substances such as forsterite and steatite of talc-$MgO$-$BaTiO_3$ system, $BaO$-$TiO_2$-$NdO$ system or $Mg.SiO_2$ system. Preferably, by using titanium complex oxide of ilmenite crystal structure, the sensing element can be used either for alternating current or direct current. Incidentally, in the case of the ceramics mainly composed of titanium complex oxide of ilmenite crystal structure, the same may be mixed with one kind or plural kinds of ceramics of other crystal structures such as perovskite type, spinel type, pyrochlore type, or tungsten bronze type, to the extent that such mixing will not unfavorably affect the characteristics of the same. Further, the same may be added with inorganic compounds such as clay, rare earth elements, $TiO_2$, $SiO_2$, $Bi_2O_3$, $ZnO$, $Fe_2O_3$, $Sb_2O_3$, $MnCO_3$, and $WO_3$. But, a material whose temperature coefficient of permitivity is within 20% at 0° C. is preferred for the reason that the frosted state and the dry state can then be distinguished more clearly. In this sense, such ceramics as composed of $MgTiO_3$ (96%) - $CaTiO_3$ (4%) is a preferred material because it exhibits an extremely small temperature coefficient of permitivity. In addition, ceramics of other crystal structure systems may also be added with a variety of additives similarly to as said for titanium complex oxide of ilmenite type crystal structure.

EXAMPLE No. 1

We prepared two $MgTiO_3$-$CaTiO_3$ system ceramic plates of the dimension of 40 mm long×6 mm wide×0.8 mm thick. The ceramics was obtained by the publicly-known calcinating process. On the surface of each plate, opposing comb-shaped gold electrodes were arranged by baking. The electrodes were made so as to have opposing side length of 7.2 mm and inter-electrode distance of 0.4 mm. And then the ceramic plates were arranged so that the electrodes thereon oppose each other at a distance of 0.3 mm.

With thus composed dry/dew/frost sensor, its impedance in each of dry, bedewed, and frosted states was measured with a voltage of 1 V (100 Hz). The results were: 110 MΩ in the dry state, 12 KΩ in the bedewed state, and 10 MΩ in the frosted state. Accordingly, it is understood that it can detect the three states, dry, bedewed, and frosted states, with a great accuracy.

Further, we subjected the sensor to cyclic changes between the bedewed and dry states and conducted a test of 1500 cycles of energizing the sensor. Even after such a test, there was no change appreciated in the impedance varying characteristic between the dry and bedewed states. Hence, it is understood that the dry/dew/frost sensor in this experiment is remarkably stable and good for many years' service.

Then, an apparatus for detecting dry, bedewed, and frosted states using the dry/dew/frost sensor of the present invention will be explained as follows.

Figure 8:
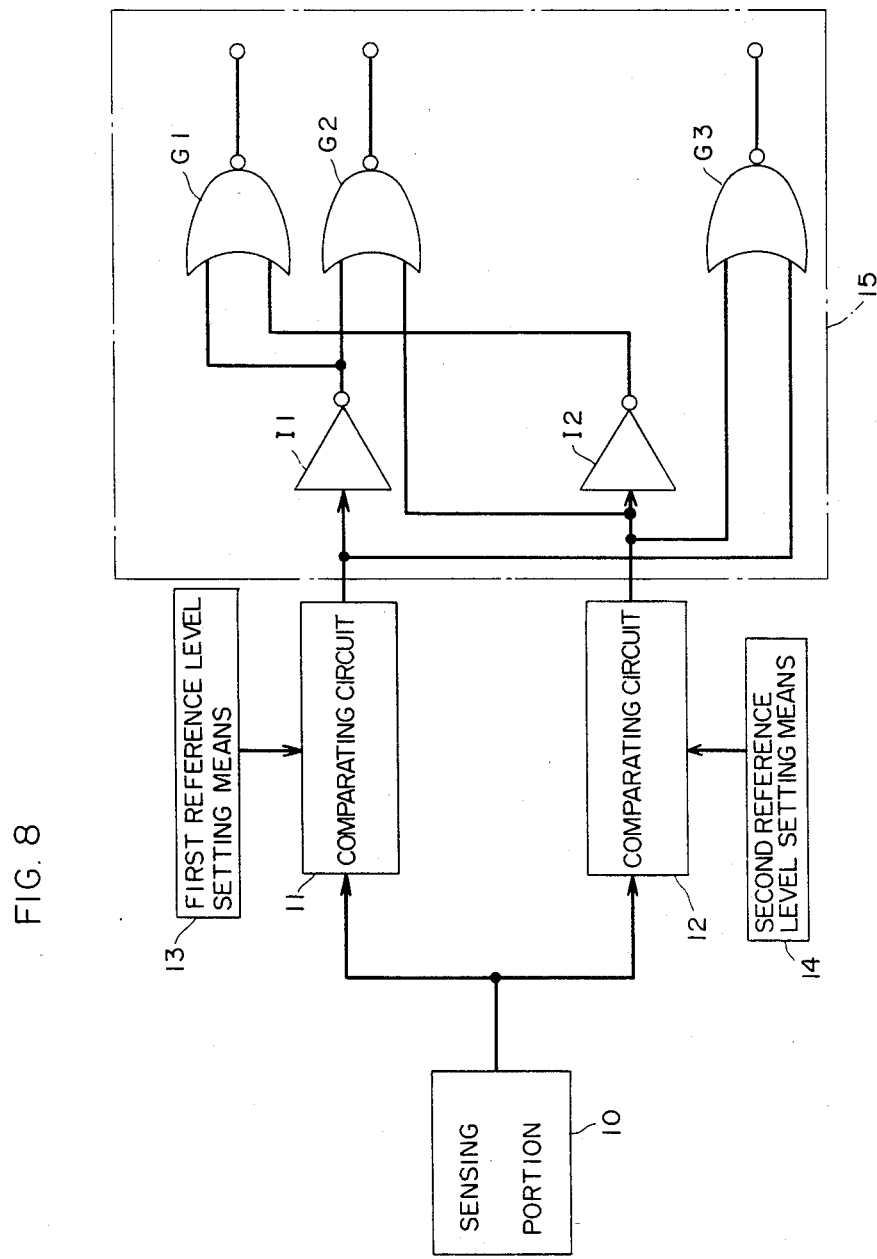
FIG. 8 is a block diagram showing an example of a dry/dew/frost sensing apparatus using the dry/dew/frost sensor of the present invention.

FIG. 8 is a block diagram to explain an example of the dry, bedewed, and frosted states detecting appartus using the dry/dew/frost sensor of the present invention. Referring to FIG. 8, the example comprises a sensing portion 10 including the dry/dew/frost sensor of the present invention, two comparing circuits 11 and 12 provided with outputs from the sensing portion 10, first reference level setting means 13 for inputting a first reference level signal as a signal to be compared to the comparing circuit 11, second reference level setting means 14 for inputting a second reference level signal as a signal to be compared to the comparing circuit 12, and a determining circuit 15 responsive to outputs from the comparing circuits 11 and 12 (a portion encircled by a chain line) for determining the state of an atmosphere, that is dry, bedewed or frosted state.

The sensing portion 10 outputs a signal corresponding to the impedance which varies in three states, or dry, bedewed and frosted states, as shown in FIG. 1. The output from the sensing portion 10 is divided to be provided to the first comparing circuit 11 as first comparing means and the second comparing circuit 12 as second comparing means. To the first comparing circuit 11 is inputted the first reference level signal by the first reference level setting means. The first reference level of the signal is set between the impedance of the sensing portion 10 in the bedewed state and the impedance of the sensing portion 10 in the frosted state as apparently seen from FIG. 1. The first comparing circuit 11 compares the impedance of the sensing portion 10 with the first reference level, and outputs a high level signal when the impedance of the sensing portion 10 is higher than the first reference level and outputs a low level signal when the impedance of the sensing portion 10 is lower than the same. On the other hand, to the second comparing circuit 12 is inputted the second reference level signal by the second reference level setting means. The second reference level of the signal is set between the impedance of the sensing portion 10 in the dry state and the impedance of the sensing portion 10 in the frosted state as is apparent from FIG. 1. The second comparing circuit 12 compares the impedance of the sensing portion 10 with the second reference level, and outputs a high level signal when the impedance of the sensing portion 10 is higher than the second reference level and outputs a low level signal when the impedance of the sensing portion 10 is lower than the same.

As described above, the first and second comparing circuits 11 and 12 each output a high level or low level signal responsive to the variations in the impedance of the sensing portion 10. The outputs from the respective comparing circuits 11 and 12 are to be shown in the following Table 1, as apparent from the relationship shown in FIG. 1. In the Table 1, H represents a high level signal and L represents a low level signal.

TABLE 1

|  | first comparating circuit 11 | second comparating circuit 12 |
| --- | --- | --- |
| dry state | H | H |
| frosted state | H | L |
| bedewed state | L | L |

The outputs from the first and second comparing circuits 11 and 12 are provided to the determining circuit 15. The determining circuit 15 comprises two inverters I1, I2, and three NOR gates G1, G2, G3. The output from the first comparing circuit 11 is applied to the input terminal of the inverter I1 and one of the input terminals of the NOR gate G3. The output from the inverter I1 is applied to one of the input terminals of each of the NOR gates G1 and G2. On the other hand, the output from the second comparing circuit 12 is applied to the input terminal of the inverter I2, the other terminal of the NOR gate G2 and the other terminal of the NOR gate G3. The output from the inverter I2 is applied to the other input terminal of the NOR gate G1. Meanwhile, the determining circuit 15 employs positive logic.

The determining circuit structured as described above determines each of the three states, or dry, bedewed and frosted states, in the following way.

On the occasion of the dry state, as apparent from Table 1, each of the comparing circuit 11 and 12 outputs a high level signal. The high level signal from the first comparing circuit 11 is applied to the inverter I1 and NOR gate G3. The high level signal inputted to the inverter I1 is inverted to a low level signal and then applied to the NOR gates G1 and G2. On the other hand, the high level signal from the second comparing circuit 12 is applied to the inverter I2, NOR gate G2 and NOR gate G3. The high level signal inputted to the inverter I2 is inverted to a low level signal to be applied to the NOR gate G1. As described above, on the occasion of the dry state, only the NOR gate G1 is provided with low level signals at its both input terminals. Accordingly, only the NOR gate G1 outputs a high level signal. Likewise, on the occasion of the sensing portion 10 being in the frosted state, as apparent from Table 1, since the first comparing circuit 11 outputs a high level signal and the second comparing circuit 12 outputs a low level signal, only the NOR gate G2 is provided with low level signals at its both input terminals. Accordingly, only the NOR gate G2 outputs a high level signal. Further, on the occasion of the sensing portion 10 being in the bedewed state, since both the first and second comparing circuits 11 and 12 output low level signals, only the NOR gate G3 is provided with low level signals at its both input terminals; accordingly, only the NOR gate G3 outputs a high level signal.

As seen apparently from the above description, the NOR gate G1 outputs a signal on the occasion of the dry state, the NOR gate G2 outputs a signal on the occasion of the frosted state, and the NOR gate G3 outputs a signal on the occasion of the bedewed state. Accordingly, it becomes possible to detect each of the three states, or dry, bedewed and frosted states.

Figure 9:
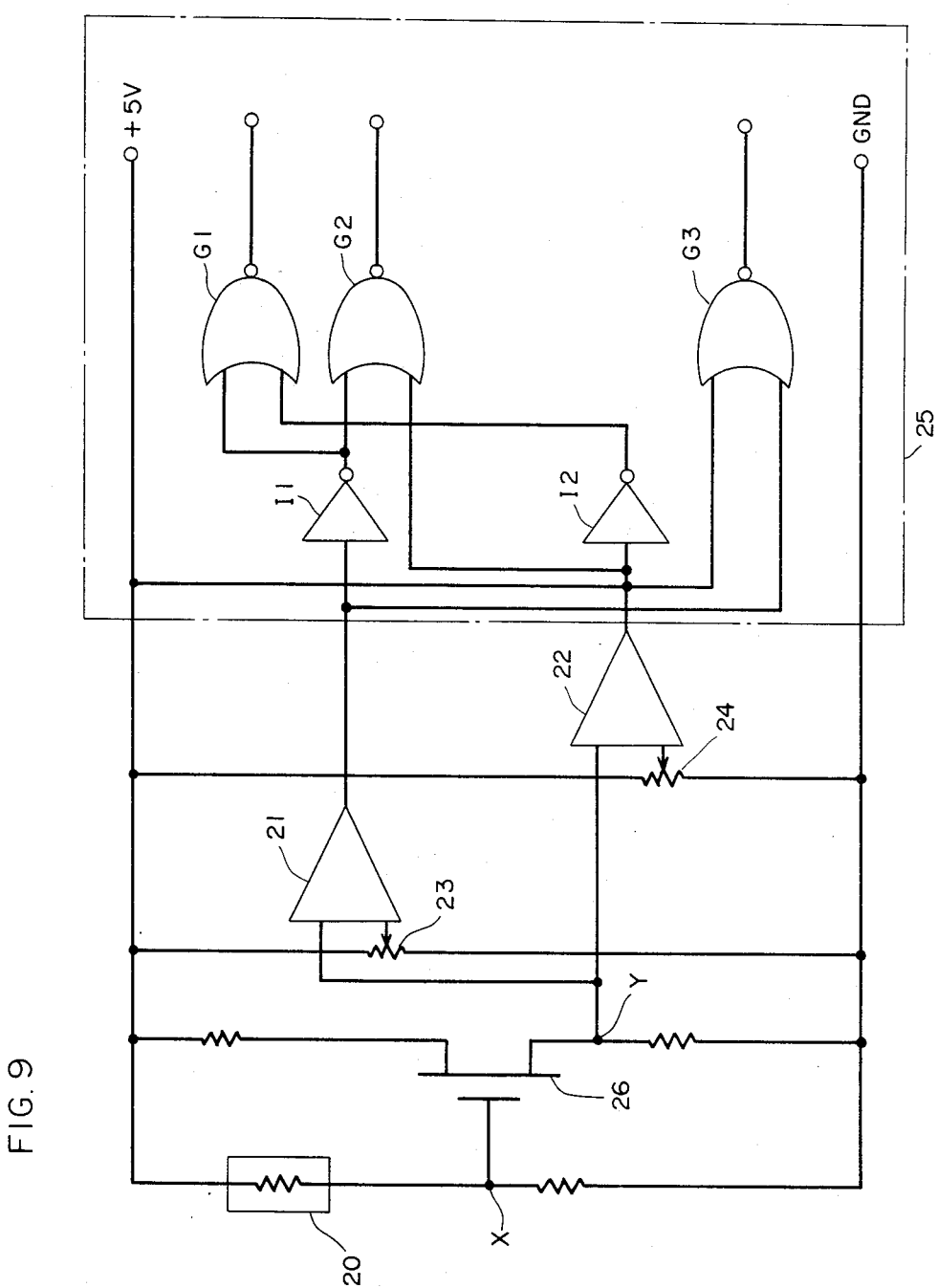
FIG. 9 is a circuit diagram more concretely illustrating the block diagram shown in FIG. 8.
Figure 10:
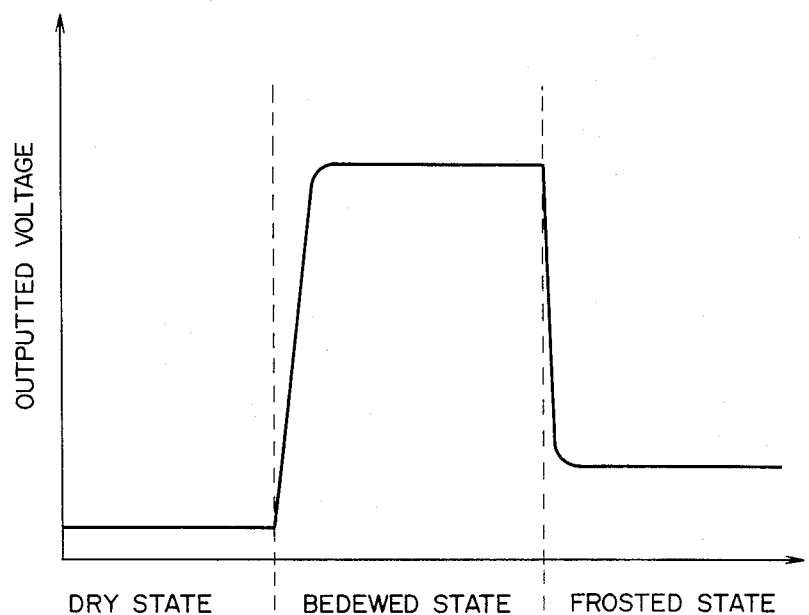
FIG. 10 is a graph showing output voltages at the connection point X in the circuit in FIG. 9.
Figure 11:
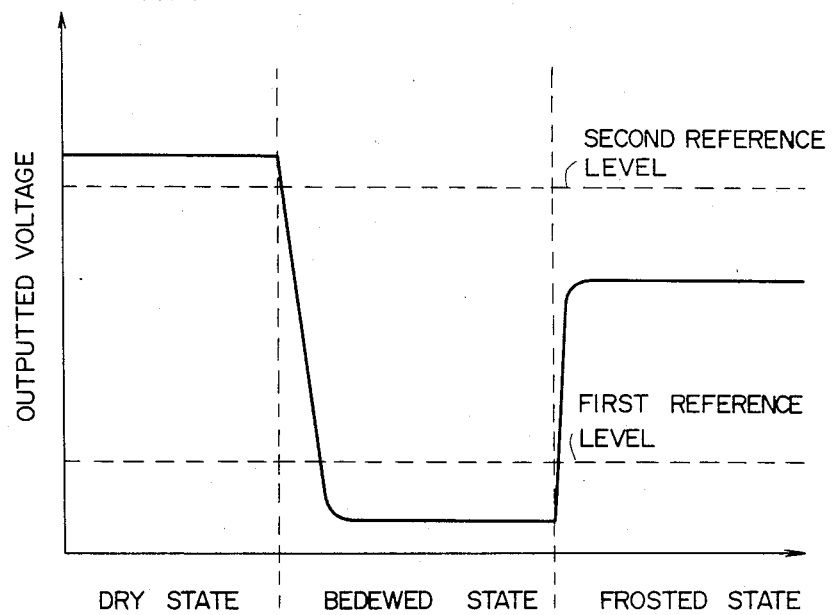
FIG. 11 is a graph showing output voltages at the connection point Y in the circuit in FIG. 9.

FIG. 9 is a circuit diagram for more specifically illustrating the dry, bedewed and frosted states detecting apparatus shown in FIG. 8. FIGS. 10 and 11 are graphs for explaining the operation of the circuit in FIG. 9.

The circuit shown in FIG. 9 basically comprises the dry/dew/frost sensor of the present invention 20, an MOS-FET 26, comparators 21 and 22, and a determining circuit 25 (a portion encircled by a chain line) which is similar to the one shown in FIG. 8. The impedance of the dry/dew/frost sensor 20 varies in the three states, or dry, bedewed and frosted states, as shown in FIG. 1. The variations in the impedance on the dry/dew/frost sensor 20 are inputted, in the form of variations in the voltage, to the gate terminal of the MOS-FET 26. The input is amplified and inverted by the MOS-FET 26 to be inputted to operation amplifiers 21 and 22 as comparators. To the operation amplifiers 21 and 22 are inputted the first and second reference level voltages through variable resistors 23 and 24, respectively. The outputs from the operation amplifiers 21 and 22 are applied to the determining circuit 25. Since the configuration of the determining circuit 25 is similar to that of the determining circuit 15 shown in FIG. 8, the corresponding components are denoted by the same reference numerals as those in FIG. 8, and therefore, explanation of the components is omitted here.

In the circuit in FIG. 9 as described in the above, since the impedances of the dry/dew/frost sensor 20 vary with the changes in three states, or dry, bedewed, and frosted states, the dry/dew/frost sensor 20 will output varying voltages dependent on the variations in the impedance. The variations in the voltage at the connection point X is shown in FIG. 10. The outputted voltage from the dry/dew/frost sensor 20 is amplified and inverted by the MOS-FET 26 and then outputted therefrom. The outputted voltage, that is the voltage at the connection point Y in FIG. 9, is shown in FIG. 11. As apparent from FIG. 11, the outputted voltage at the connection point Y has the maximum value in the dry state, the minimum value in the bedewed state, and the medium value in the frosted state. The outputted voltage from the MOS-FET 26 is inputted to the operation amplifiers 21 and 22. On the other hand, to the operation amplifiers 21 and 22 are inputted the first and second reference level voltages, respectively, whose levels are set through the variable resistors 23 and 24, respectively. Thus values of the first and second reference level voltages are selected as shown in FIG. 11. More specifically, the value of the first reference level voltage is selected between those of the outputted voltage in the frosted state and the outputted voltage in the bedewed state, and the value of the second reference level voltage is selected between those of the outputted voltage in the dry state and the outputted voltage in the frosted state. The operation amplifiers 21 and 22 compare the outputted voltage of the MOS-FET 26 with each of the first reference level voltage and the second reference level voltage. Thus, the variations in the impedance of the dry/dew/frost sensor 20 are compared in the form of the variations in the voltage. Each of the operation amplifiers 21 and 22 outputs a high level signal when the outputted voltage from the MOS-FET 26 is higher than the respective reference level voltage and outputs a low level signal when the outputted voltage is lower than the same. The outputted signals from the operation amplifiers 21 and 22 become identical to the true output values shown in Table 1 that were given with reference to the circuits 11 and 12 in FIG. 8. The outputted signals from both the operation amplifiers 21 and 22 are inputted to the determining circuit 25, whereas, since the operation of the determining circuit 25 is similar to that of the determining circuit 15 in FIG. 8, the explanation is omitted here.

Each of the circuits shown in FIGS. 8 and 9 is merely one example of the apparatus for detecting dry, bedewed, and frosted states using the dry/dew/frost sensor of the present invention. Accordingly, it is pointed out that the first and second comparing circuits and the determining circuit can be modified in various ways within the scope that can be reached easily by a person skilled in the art.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A dry/dew/frost sensor, comprising:
   (A) a first sensor unit including:
      (1) a first ceramic substrate having a permittivity which is less than the permittivity of ice; and
      (2) a first pair of electrodes formed on a first surface of said first ceramic substrate and being electrically insulated and spaced apart from one another in a predetermined pattern;
   (B) a second sensor unit including:
      (1) a second ceramic substrate having a permittivity which is less than the permittivity of ice; and
      (2) a second pair of electrodes formed on a first surface of said second ceramic substrate and being electrically insulated and spaced apart from one another in a pattern similar to said predetermined pattern; and
   (C) means for mounting said first and second substrate with said first surfaces of said substrate and said first and second pairs of electrodes facing each other and being spaced insulatively apart from one another so as to define a predetermined open space between said first surfaces of said substrates, whereby the impedance of said sensor will change to different values when in a dry state, a frosted state and a bedewed state.

2. The dry/dew/frost sensor of either claim 1, wherein the impedance between said electrodes of said first pair of electrodes is determined primarily by the resistance and permittivity of said first substrate when said first surface of said first substrate is in the dry state, is determined primarily by the permittivity of ice when said first surface of said first substrate is in the frosted state, and is determined primarily by ionic conductors in water when said first surface of said first substrate is in the bedewed state, and wherein the impedance between the electrodes of said second pair of electrodes is determined primarily by the resistance in permittivity of said second substrate when said first surface of said second substrate is in the dry state, is determined primarily by the permittivity of ice when said first surface of second substrate is in the frosted state and is determined primarily by ionic conductors in water when said first surface of said second substrate is in the bedewed state.

3. The dry/dew/frost sensor of either claim 1 or 2, wherein said first surfaces are each planar surfaces which lie generally parallel to one another.

4. The dry/dew/frost sensor of claim 3, wherein said first and second substrates are ceramic plates.

5. The dry/dew/frost sensor of claim 1, further including a first output lead electrically coupled to one said electrode of each of said first and second pairs of electrodes and a second output lead electrically coupled to the remaining electrode of each of said first and second pairs of electrodes, whereby the impedance between said leads is at a maximum value when the said first surfaces are in the dry state, is at a middle value, lower than said maximum value, when said first surfaces are in a frosted state and is at a minimum value, less than both said maximum and middle values, when said first surfaces are in a bedewed state.

6. The dry/dew/frost sensor of claim 5, further comprising means for determining the impedance between said first and second leads and for generating output signals indicative of whether said first surfaces are in the dry, bedewed or frosted states.

7. The dry/dew/frost sensor of claim 6, wherein said means for determining comprises:
(A) first reference level setting means for setting a first reference level which resides between said middle value and said minimum value;
(B) second reference level setting means for selecting a second reference level which resides between said middle value and said maximum value;
(C) a first comparator for comparing said first reference level with the impedance between said first and second leads and for generating a first signal indicative thereof;
(D) a second comparator for comparing said second reference level with the impedance between said first and second leads and for generating a second signal indicative thereof; and
(E) a determining circuit for:
  (1) generating a first output signal indicating a dry state when said first signal indicates that the impedance between said first and second leads is higher than first said reference level and said second signal indicates that the impedance between said first and second leads is higher than said second reference level;
  (2) for generating a second output signal indicating the frosted state when said first signal indicates that the impedance between said first and second leads is higher than first said reference level and said second signal indicates that the impedance between said first and second leads is lower than said second reference level; and
  (3) for generating a third output signal indicating the bedewed state when said first signal indicates that the impedance between said first and second leads is lower than said first reference level and said second signal indicates that the impedance between said first and second leads is lower than said second reference level.

* * * * *